(12) United States Patent
Chatellier et al.

(10) Patent No.: US 7,415,865 B2
(45) Date of Patent: Aug. 26, 2008

(54) DETERMINING THE EXTENT OF A LATERAL SHADOW ZONE IN AN ULTRASOUND INSPECTION METHOD

(75) Inventors: Jean-Yves Chatellier, Arcueil (FR); Richard Coulette, Gentilly (FR)

(73) Assignee: Snecma, Paris (FR)

( * ) Notice: Subject to any disclaimer, the term of this patent is extended or adjusted under 35 U.S.C. 154(b) by 301 days.

(21) Appl. No.: 11/315,041

(22) Filed: Dec. 23, 2005

(65) Prior Publication Data

US 2006/0179947 A1    Aug. 17, 2006

(30) Foreign Application Priority Data

Jan. 6, 2005   (FR) .................................. 05 00099

(51) Int. Cl.
*G01N 29/30* (2006.01)
(52) U.S. Cl. .......................................... 73/1.86; 73/620
(58) Field of Classification Search .................. 73/1.82, 73/1.86, 620, 629
See application file for complete search history.

(56) References Cited

U.S. PATENT DOCUMENTS

| 3,969,926 A | | 7/1976 | Walker et al. | |
|---|---|---|---|---|
| 4,453,408 A | * | 6/1984 | Clayman | 73/1.86 |
| 5,054,310 A | * | 10/1991 | Flynn | 73/1.86 |
| 5,565,627 A | * | 10/1996 | Dorr | 73/599 |

FOREIGN PATENT DOCUMENTS

FR       2 806 162       9/2001

* cited by examiner

*Primary Examiner*—John E Chapman
(74) *Attorney, Agent, or Firm*—Oblon, Spivak, McClelland, Maier & Neustadt, P.C.

(57) ABSTRACT

A method of determining the extent of a lateral shadow zone corresponding to an edge of a part in a method of inspecting the part in immersion by means of an ultrasound beam, the method consisting in determining the extent of the shadow zone from the edge of the part by measuring the effective section of the ultrasound beam at the surface of the part, and in determining said effective section from variations in the amplitude of an echo of the beam as a function of the distance between the axis of the beam and the edge of the part.

17 Claims, 5 Drawing Sheets

DETERMINING THE EXTENT OF A LATERAL SHADOW ZONE IN AN ULTRASOUND INSPECTION METHOD

The present invention relates to determining the extent of a lateral shadow zone corresponding to an edge of a part, in a method of using an ultrasound beam to inspect the part while it is immersed.

BACKGROUND OF THE INVENTION

Inspecting a part in immersion by means of an ultrasound beam serves to detect defects in the part such as, for example: bubbles, inclusions, etc.

The technique is implemented in a vessel filled with an acoustic coupling liquid, such as water, having an ultrasound generator, such as an electroacoustic transducer, that is immersed in the water and that is oriented towards the part for inspection perpendicularly to a surface thereof, the transducer being spaced apart from said surface of the part by a depth of water referred to as the "water column".

The transducer emits a beam of ultrasound waves which is partially reflected on the surface of the part and partially transmitted to the inside of the part, the transmitted ultrasound waves possibly encountering on their trajectories internal defects that are capable of reflecting them. The echoes coming from such reflections are picked up by the transducer, which also acts as a receiver, and the amplitudes of the echoes represent the magnitudes of the detected defects.

In practice, inspecting a part includes relative movement between the part and the transducer or a series of transducers so as to scan the part by means of one or more ultrasound beams.

When the ultrasound beam is moved progressively towards an edge of the part, an ever-increasing fraction of the section of the beam at the surface of the part lies beyond the edge of the part such that a fraction of the energy of the beam is emitted outside the part and will not be reflected by a defect in that portion of the part that is covered by the beam.

Consequently, a defect will be detected in the form of an echo, but of amplitude that becomes progressively weaker as the beam approaches the edge of the part, with said amplitude dropping to zero when the beam no longer encounters the part.

The portion of the part in which the echo amplitude on the beam being reflected by a defect decreases because of this phenomenon is a zone that cannot be inspected by known methods and is referred to as a "shadow zone" or as a "lateral dead zone" of the part. The known technique does not make it possible to determine the exact extent of said dead zone at arbitrary depth in the part, and it is therefore necessary as a precaution to give it a maximum value, e.g. 12 millimeters (mm) even though it might be much smaller in reality, e.g. half that, which corresponds to ignoring a relatively large amount of matter.

OBJECTS AND SUMMARY OF THE INVENTION

A particular object of the invention is to determine a lateral shadow zone of a part in an ultrasound inspection method, where such determination is accurate, reliable, and easy to implement.

To this end, the invention provides a method of determining the extent of a lateral shadow zone corresponding to an edge of a part, in a method of inspecting the part in immersion by means of at least one ultrasound beam emitted by a transducer oriented perpendicularly to a surface of the part, the method consisting in determining the extent of the shadow zone from the edge of the part by measuring the effective section of the ultrasound beam at the surface of the part, the extent of the shadow zone for a determined distance between the transducer and the surface of the part being equal to the radius of the effective section of the beam at the surface of the part, and in determining said effective section from variations in the amplitude of an echo of the beam as a function of the distance of the axis of the beam from the edge of the part.

The invention is based on the observation that the lateral shadow zone is associated not with the −6 decibel (dB) diameter of the focal spot of the beam, which varies hyperbolically with depth in the part, but with the section of an energy cone emitted by the transducer and of diameter or radius that varies linearly with depth in the part.

The section of the energy cone, or the effective section of the beam can be determined simply from variations in the amplitude of an echo of the beam as a function of the distance of the axis of the beam from the edge of the part.

In a first implementation of the invention, the distance between the transducer and the surface of the part is constant, so the effective section of the beam at the surface of the part is determined by measuring the variation in the echo amplitude at the reflection of the beam on the surface of the part as a function of the distance between the axis of the beam and the edge of the part.

For example, the method consists: in measuring the distance $d_1$ between the axis of the beam and the edge of the part from which the echo amplitude begins to decrease when the distance $d_1$ from the edge of the part decreases; in measuring the distance $d_2$ between the axis of the beam and the edge of the part at which said amplitude becomes zero; and in obtaining the size of the shadow zone from the edge of the part by calculating the value $(d_1+d_2)/2$. In practice, the distance between the axis of the beam and the edge of the part is measured when the echo amplitude is equal to a small fraction, e.g. a few percent, of the maximum value of said amplitude, and the distance $d_2$ between the axis of the beam and the edge of the part at which said amplitude becomes zero is determined by extrapolation.

In a second implement of the invention, the transducer is oriented perpendicularly to the surface of the part away from the shadow zone, and a beam deflector element is moved in translation on the surface of the part along an axis that intersects the axis of the ultrasound beam, the method consisting in identifying the positions of said elements for which the echo amplitude at the reflection of the beam on the surface of the part varies between a maximum value and a zero value.

Advantageously, under such circumstances, the invention also proposes aligning the emission axis of the transducer on a calibration hole formed in the part outside the shadow zone, and in measuring the variation in the echo amplitude at the reflection of the beam on the end wall of the calibration hole during progressive interception of the beam by the deflector element.

By way of example, the deflector element is a prism presenting at least one sloping reflection face, e.g. sloping at 45° relative to the surface of the part and to the axis of the beam. The method can consist in identifying two positions of the prism that are diametrically opposite about the axis of the ultrasound beam and for which the echo amplitude at the reflection of the beam on the surface of the part begins to decrease from a maximum value as the prism approaches the axis of the beam, and in calculating half the distance between those two positions in order to obtain the extent of the lateral shadow zone.

In a third implementation of the invention, the method consists in determining the size of the lateral shadow zone on a calibration part having identical flat-ended holes formed at the same depth and at different distances from the edge of the part, one of the holes being outside the shadow zone and the other holes being in said zone, in aligning the transducer on each hole in succession, and in measuring the echo amplitude at the reflection of the beam on the end wall of the hole, in plotting the curve of variation in said amplitude between a maximum value and a zero value as a function of the distance between the axes of the holes and the edge of the part, and in deducing the size of the shadow zone as being equal to the distance value at which said amplitude begins to decrease when the distance between the axes of the holes and the edge of the part decreases.

In a fourth implementation of the invention, the method consists in constructing a straight line showing variation in the radius of the effective section of the ultrasound beam as a function of the penetration depth of said beam into the part, starting from an initial radius value corresponding to zero distance between the transducer and the part for which the radius of the effective section at the surface of the part is equal to the radius of the transducer, and a final value of the radius at a depth in the part corresponding to the focal length of the transducer. Thereafter, the method consists, for a given distance between the transducer and the part, and for a given depth in the part, in calculating the extent of the lateral shadow zone as the difference between the radius of the effective section of the beam at the surface of the part and the radius of the effective section at the depth under consideration. In practice, it is possible to determine the final value of the radius of the effective section of the beam by placing the transducer at a distance from the surface of the part that corresponds to its focal length, and by measuring the radius of the effective section of the beam at the surface of the part as specified above.

BRIEF DESCRIPTION OF THE DRAWINGS

Other characteristics, details, and advantages of the invention appear on reading the following description made by way of non-limiting example and with reference to the accompanying drawings, in which.

MORE DETAILED DESCRIPTION

Figure 1:
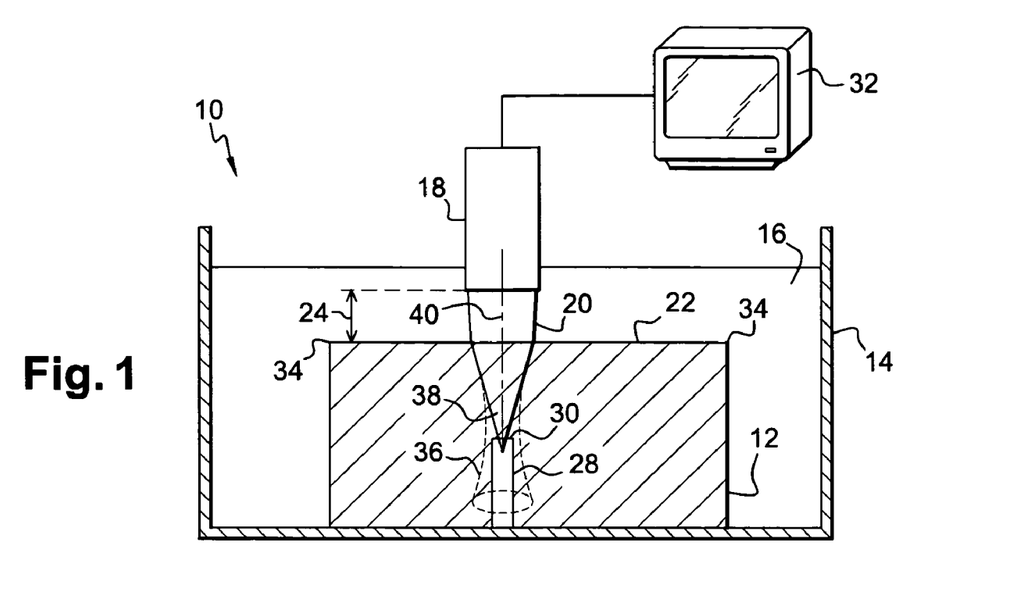
FIG. 1 is a diagrammatic section view of a device for inspecting a part in immersion by means of an ultrasound beam.

FIG. 1 is a diagram showing a device 10 for inspecting a part 12 in immersion by means of an ultrasound beam, the device comprising a vessel 14 filled with water 16 in which the part 12 for inspection and an electroacoustic transducer 18 are both immersed, the transducer serving to generate an ultrasound beam 20 oriented perpendicularly to a surface 22 of the part 12, the transducer 18 being spaced apart from said surface 22 by a depth of water referred to as the "water column" 24.

The transducer 18 is connected to control means (not shown), such as a microcomputer, and to pulse generator means.

Some of the emitted ultrasound waves is reflected at the surface 22 of the part and the remainder are transmitted into the inside of the part, with the ultrasound waves propagating within the part 12 possibly encountering on their trajectory a defect that is capable of reflecting them. A defect might be constituted, for example, by a bubble, an inclusion, etc., and one such defect is represented diagrammatically by a hole 28 having a flat top end wall 30 situated towards the surface 22 of the part while the hole opens out into the bottom surface of the part 12.

Echoes due to ultrasound waves being reflected on the surface 22 of the part and/or on defects within the part 12 are picked up by the transducer 18 and are recorded and displayed on means 32 for displaying their amplitudes, such as an oscilloscope, which means are connected to the transducer 18.

The method of the invention makes it possible to determine accurately the extent of a dead zone or lateral shadow zone corresponding to an edge 34 of the part 12, this shadow zone being a portion of the part 12 in which the amplitude of the echo due to the beam being reflected on a defect decreases because of the above-described phenomenon.

In the invention, the lateral shadow zone is associated not with the −6 dB size of the focal spot of the beam 20, which varies hyperbolically with depth in the part 12, as shown at 36, but with the section of an energy cone 38 emitted by the transducer 18 and of radius that varies linearly with depth in the part.

The extent of the shadow zone can be associated with the size of the effective section of the beam 20 at the surface 22 of the part, and this effective section can be determined from variations in the amplitude of an echo of the beam 20 as reflected on the surface of the part as a function of the distance of the axis 40 of the beam 20 from the edge 34 of the part.

Figure 2:
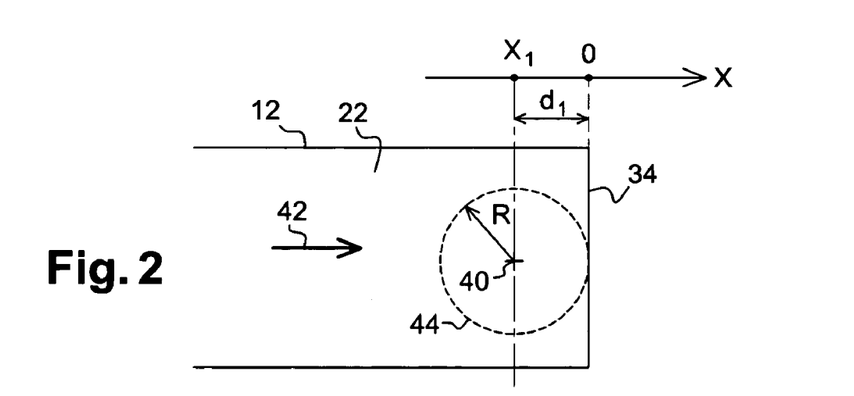
FIGS. 2 to 4 are diagrammatic views of a surface of the part showing a first implementation of the method of the invention for determining the extent of a lateral shadow zone.
Figure 3:
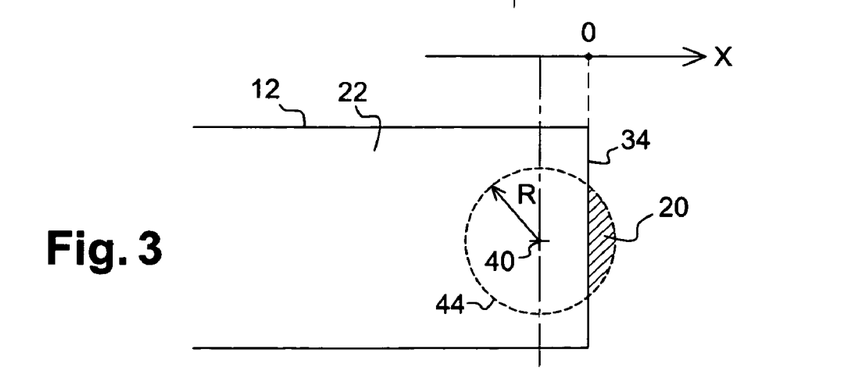
Figure 4:
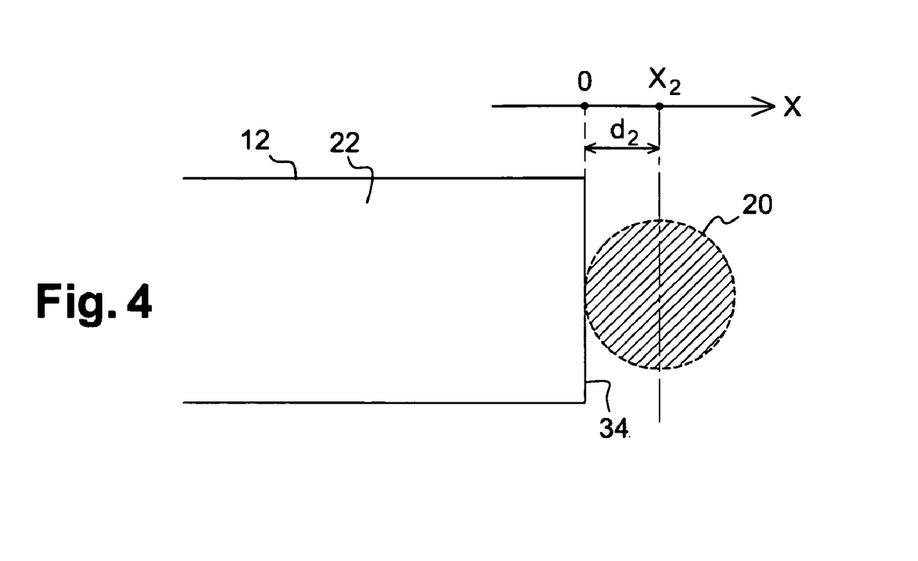

In a first implementation shown in FIGS. 2 to 4, the transducer 18 is spaced apart from the surface 22 of the part by a water column 24 having a predetermined value, it is oriented perpendicularly to the surface 22 of the part, and it is at a sufficient distance from its edges. The echo amplitude at the reflection of the beam 20 on the surface 22 of the part is measured. In practice, this amplitude can be adjusted to be 80% of the height of the screen of the display means 32 for making it easier to display variation in echo amplitude.

The transducer 18 is then moved in translation over the part 12 along arrow 42 towards the edge 34 of the part and parallel to the surface 22 of the part, and the position is identified at which the echo amplitude at the reflection on the surface 22 of the part begins to decrease from the maximum value, followed by the position in which this amplitude becomes substantially zero.

The position of the transducer 18 is determined from the position of the axis 40 of the beam 20 on an axis X extending along the arrow 42 with the origin being situated at the edge 34 of the part.

In FIG. 2, the axis 40 of the beam is in a position $X_1$ where the edge 34 of the part is tangential to the effective section 44 of the beam 20 at the surface of the part, and the echo amplitude at the reflection of the beam on the surface 22 of the part has a value that is substantially equal to the maximum value. The distance $d_1$ between the axis 40 of the beam and the edge 34 of the part is defined as being equal to $|X_1|$.

In FIG. 3, the transducer 18 has been moved into a position where a fraction of the energy of the beam 20 is emitted outside the part 12, such that the echo amplitude at the reflection of the beam on the surface 22 of the part has a value that is less than the maximum value.

In FIG. 4, the transducer 18 has been moved to a position $X_2$ for which the beam is emitted outside the part 12, so the effective section of the beam 20 in the plane of the surface 22 of the part is externally tangential to the edge 34 such that the echo amplitude at the reflection of the beam on the surface 22 of the part is substantially zero. The distance $d_2$ between the axis 40 of the beam and the edge 34 of the part is defined as being equal to $|X_2|$.

Figure 5:
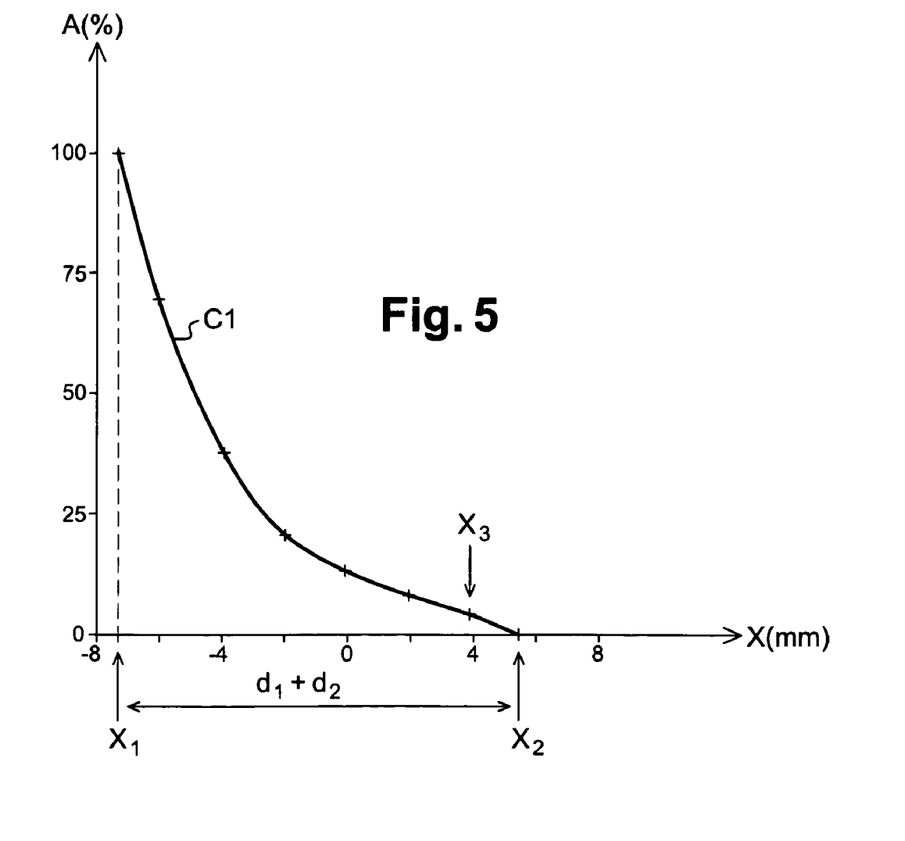
FIG. 5 is a graph showing how the amplitude of an echo of the beam varies as a function of the position of the axis of the beam relative to the edge of the part.

FIG. 5 is a graph showing the curve C1 of variation in the echo amplitude at the reflection of the beam 20 on the surface 22 of the part as a function of the position of the axis 40 of the beam relative to the edge 34 of the part along the axis X. To construct this curve, values are taken of the echo amplitude for the positions $X_1$ and $X_2$ and for some number of intermediate positions.

The amplitude decreases from its maximum value corresponding to the position $X_1$ down to a value that is zero or substantially zero corresponding to the position $X_2$.

The size of the shadow zone is equal to the radius R of the effective section 44 of the beam 20 at the surface of the part, and is defined by the expression:

$$R=(d_1+d_2)/2$$

In the example shown in FIG. 5, for a water column 24 having a value of 40.8 mm between a Panametrics V322-239 440 transducer having a focal length F=8 inches (in) and the surface 22 of the part 12, the dimension of the shadow zone is equal to:

$$R=(d_1+d_2)/2=(|X_1|+|X_2|)/2=(7.26 \text{ mm}+5.6 \text{ mm})/2=2=6.43 \text{ mm}$$

In practice, the values of $X_1$ and more particularly of $X_2$ can be difficult to obtain accurately. They can be determined by extrapolation using appropriate means for calculating linear or polynomial regression on the curve that is obtained experimentally.

In particular, the echo amplitude is not measured for the position $X_2$, but for a nearby position $X_3$, e.g. where the amplitude is equal to 5% of its maximum value. The curve C1 is then extended to $X_2$ by extrapolation.

Figure 6:
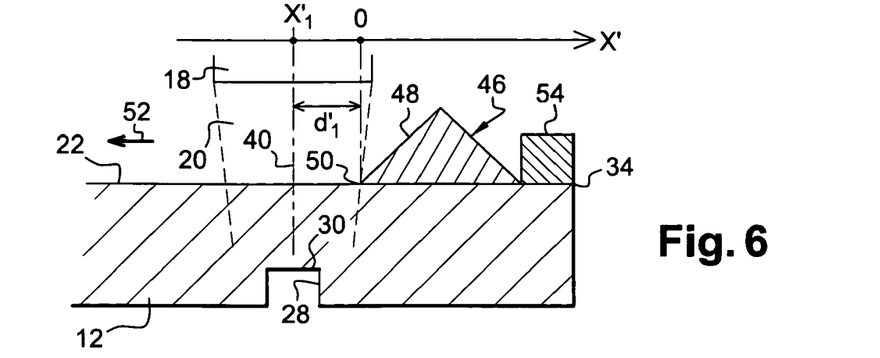
FIGS. 6 and 7 are diagrammatic section views of the part showing a second implementation of the method of the invention.
Figure 7:
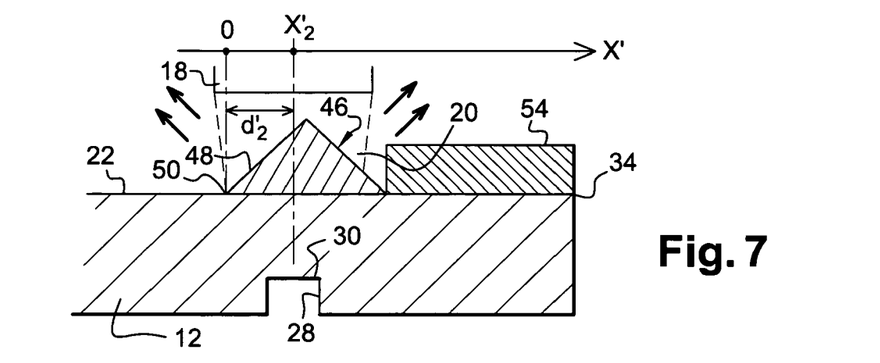

In a second implementation of the invention, shown in FIGS. 6 and 7, the transducer 18 is spaced apart from the surface 22 of the part by a water column 24 of predetermined value, and it is oriented perpendicularly to the surface 22 of the part. The echo amplitude at the reflection the surface 22 outside the shadow zone is measured and its display is adjusted to 80% of the height of the screen.

An element 46 for deflecting the beam 20 is placed on the surface 22 of the part and is moved towards the axis 40 of the beam 20 so as to deflect a fraction of the beam away from the pickup zone of the transducer 18.

In the example shown, the deflector element 46 is a prism presenting at least one sloping reflection face 48, e.g. sloping at 45° relative to the surface 22 of the part and to the axis 40 of the beam, said face 48 being terminated by an edge 50 in contact with the surface 22 of the part.

The prism 46 is moved along the arrow 52 along an axis that intersects the axis 40 of the ultrasound beam 20 between two extreme positions, in one of which the prism 46 is tangentially outside the effective section of the beam on the surface 22 of the part, as shown in FIG. 6 where the prism 46 is in the position $X'_1$, and in the other of which it deflects the beam 20 entirely, as shown in FIG. 7 where the prism is in the position $X'_2$, with $d'_1$ and $d'_2$ being respectively the values of $|X'_1|$ and $|X'_2|$.

By way of example, the prism 46 is positioned by means of spacers 54 interposed between the prism 46 and the edge 34 of the part, the spacers 54 being of very accurate dimensions and serving to position the edge 50 of the prism 46 relative to the axis 40 of the beam with very great precision, e.g. of micrometer order.

Figure 8:
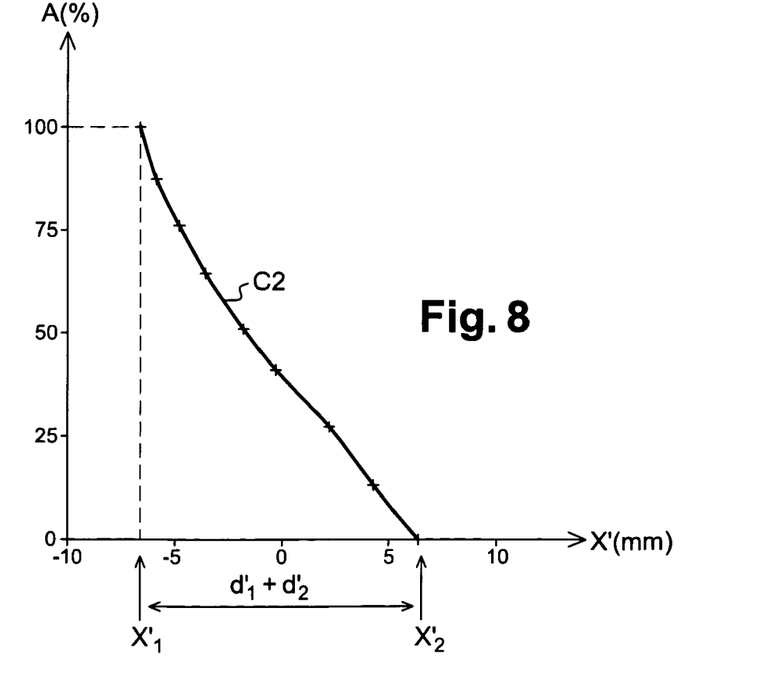
FIG. 8 is a graph showing how the amplitude of an echo of the beam varies as a function of the position of an edge of an element being moved on the surface of the part relative to the axis of the beam.

The variation in the echo amplitude at the reflection of the beam on the surface 22 of the part as a function of the position of the edge 50 of the prism relative to the axis 40 is represented by curve C2 in FIG. 8. For a water column having a value of 40.8 mm between a Panametrics V322-239 440 transducer with a focal length F=8 in and the surface 22 of the part, the dimension of the shadow zone is equal to:

$$R=(d'_1+d'_2)/2=(|X'_1|+|X'_{21}|)/2=(6.69 \text{ mm}+6.31 \text{ mm})/2=6.50 \text{ mm}$$

The values of $X'_1$ and $X'_2$ can likewise be extrapolated as described above in order to obtain greater accuracy.

In a variant, the method can consist in identifying the two positions of the edge 50 of the prism that are diametrically opposite about the axis 40 of the beam and at which the edge 50 of the prism is tangential to the effective section of the beam 20 at the surface 22 of the part, with the value of the echo amplitude at the reflection of the beam on the surface of the part being substantially at its maximum value in both these two positions.

To do this, the prim 46 is moved on the surface 22 of the part along arrow 52 to the position $X'_1$, and is then placed on the other side of the beam 20 symmetrically about the axis 40, and is moved on the surface 22 of the part in the opposite direction to the arrow 52 to a position $X''_1$, equivalent to $X'_1$.

The distance between these two positions $X'_1$ and $X''_1$ enables the size of the shadow zone to be determined, which is equal to:

$$R=(|X'_1|+|X''_1|)/2$$

In a variant, as shown in FIGS. 6 and 7, the axis 40 of the beam 20 may be aligned on a hole 28 formed in the part to a given depth and at a given distance from its edges 34 so that transducer 18 picks up the echo at the reflection of the beam on the flat end wall 30 of the hole. Under such circumstances, the amplitudes of the echo are observed for different positions of the edge 50 of the prism relative to the axis 40 of the beam, as before, and a curve is plotted showing variation analogous to the curve C2 in FIG. 8, with the extent of the shadow zone being deduced therefrom.

Figure 9:
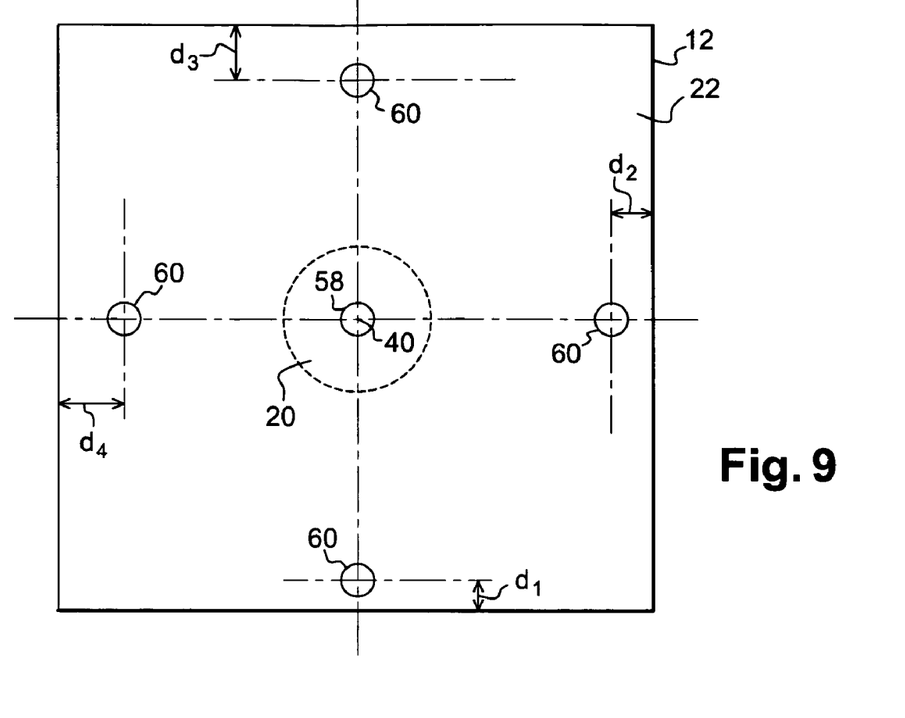
FIG. 9 is a diagrammatic view of the surface of the part, showing a third implementation of the method of the invention.

In a third embodiment of the invention shown in FIG. 9, a calibration part 12 is used having a plurality of flat-ended holes 58, 60 that are identical and formed in the part 12 to a common determined depth, with one of the holes 58 being far enough away from the edges 34 of the part to be outside the shadow zone, while the other holes 60 are close to the edges 34 of the part, their axes being at different distances from the edges 34 and lying within the shadow zone.

By way of example, the hole 58 is formed substantially in the middle of the part and the holes 60 are formed at distances $d_1$, $d_2$, $d_3$, and $d_4$ from the edges of the part that are equal respectively to 3 mm, 4 mm, 5 mm, and 6 mm.

The axis 40 of the beam is initially aligned on the hole 58 to measure the echo amplitude at the reflection on the flat top end wall of the hole 58.

Thereafter, the axis 40 of the beam 20 is aligned in succession on each of the holes 60 ad the echo amplitude at the reflection of the beam on the flat end wall of each hole 60 is measured, for the same water column 24 between the transducer and the surface of the part.

Figure 10:
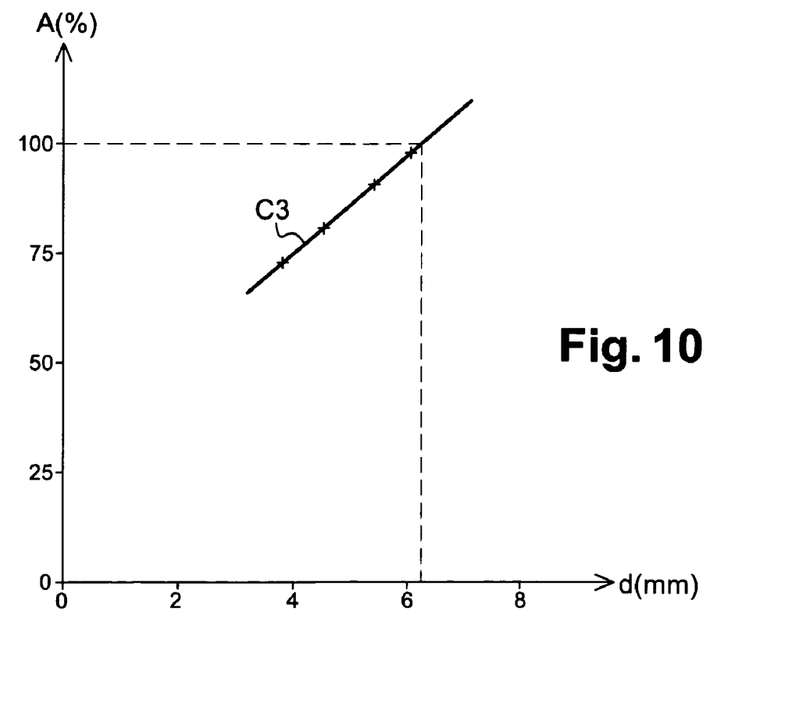
FIG. 10 is a graph showing how the amplitude of an echo of the beam varies as a function of the distance of the hole in the part from the edges thereof.

The variation in the echo amplitude as a function of the distance between the axes of said holes and the edges 34 of the part is represented by curve C3 in FIG. 10.

The size of the shadow zone is equal to the value of the distance d at which the amplitude begins to decrease from the maximum value which corresponds to the amplitude of the echo on the end wall of the hole 58, with decreasing values for the distance d. This can be determined on the graph by the abscissa of the point where the straight line obtained by linear regression through the experimental points has an ordinate value of 100%, or by extrapolating said line as described above. In the example shown, for a water column having a value of 40.8 mm between a Panametrics V322-239 440 transducer with a focal length F=8 in and the surface 22 of the part, the dimension of the shadow zone is equal to 6.31 mm.

In a fourth implementation of the invention, the radius of the effective section of the ultrasound beam 20 is determined for different penetration depths of the beam within the part 12.

The maximum value of this radius corresponds to a water volume 24 having a value of zero, and it is then equal to the radius of the effective section of the beam at the surface 22 of the part, which is equal to the radius of the transducer.

The minimum value of this radius corresponds to a penetration of the beam equal to the focal length of the transducer and is equal to the radius of the effective section of the beam at the surface of the part for a value of the water column 24 equal to the focal length of the transducer, which can be determined by the first or second implementation of the invention.

It has been found in practice that the variation in the radius of the effective section between the above-mentioned maximum and minimum values is linear. This straight line D is plotted in FIG. 11 as a function of the distance z from the transducer, where the distances z are measured in water.

Figure 11:
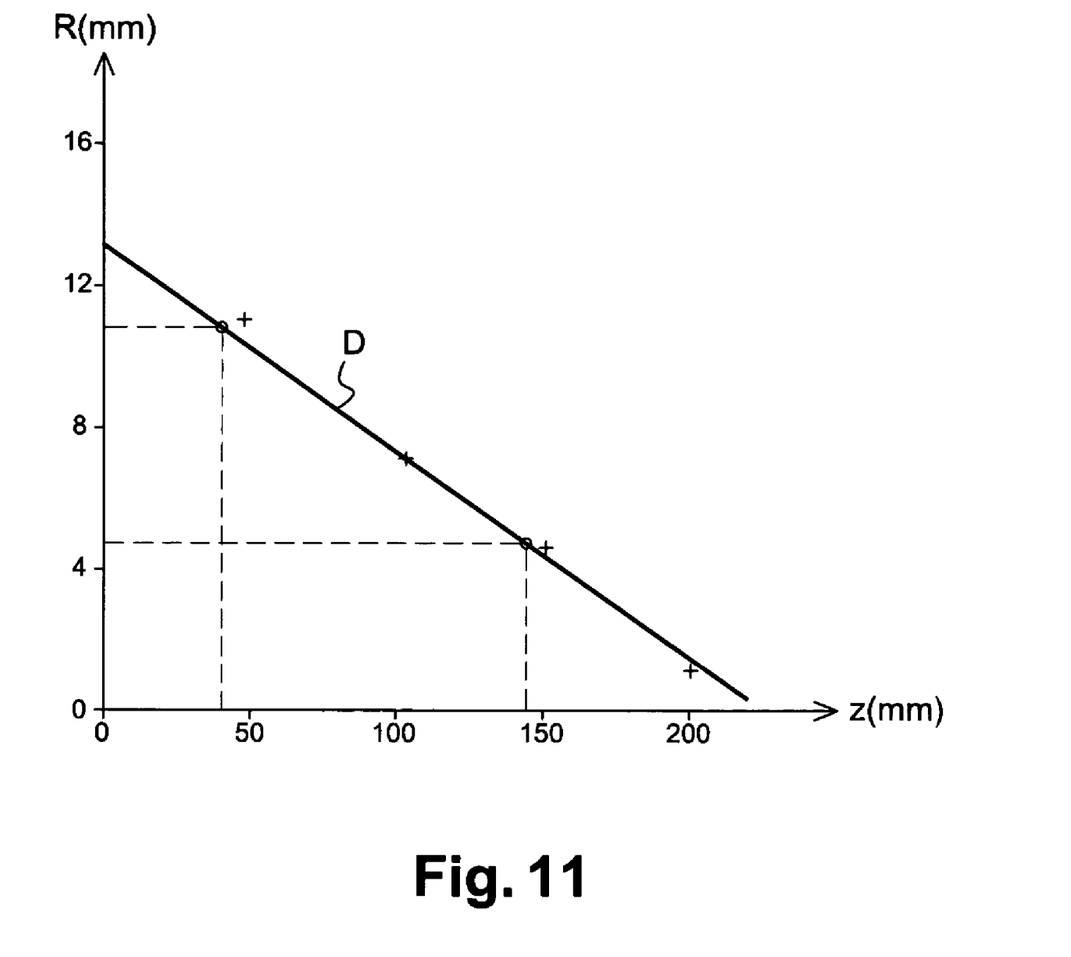
FIG. 11 is a graph showing how the radius of the effective section of the beam varies as a function of the penetration depth of the beam.

In this example, the maximum value of the effective radius is 13.1 mm and its minimum value is 1.4 mm for a Panametrics V322-239 440 transducer with a focal length F=8 in (203.2 mm) in water.

For a given value of the water column 24 and for a given depth of a hole or a defect in the part 12, this straight line makes it possible to determine the extent of the shadow zone which is equal to the difference between the radius of the effective section of the beam at the surface 22 of the part and the radius of the effective section of the beam at the depth in question.

For a water column having a value of 40.8 mm between a Panametrics V322-239 440 transducer with a focal length F=8 in and the surface 22 of the part, the axis 40 of the transducer beam is aligned with a flat-ended cylindrical hole having a diameter of 0.4 mm formed in the part 12 and at a depth of 25.4 mm from the surface 22.

The radius of the effective section of the beam at the surface 22 of the part is determined from the graph of FIG. 11 for a distance z between the effective section and the transducer 18 that is equal to the water column 24 having a value of 10.71 mm.

The radius of the effective section of the beam at the depth under consideration is determined from the graph of FIG. 11 for a distance between the effective section of the transducer equal to the above-mentioned water column value plus the depth of the hole in question converted into an equivalent distance in water, i.e. after making allowance for the different propagation speeds of the ultrasound beam 20 in the material of the part 12 and in water 16. For a part made of titanium, the ratio of the propagation speeds of an ultrasound beam is:

$$r = v_{Ti}/v_{water} = 6136.9/148.5 = 4.128$$

The equivalent distance in water of the depth under consideration is 4.128×25.4=104.85 mm, and the equivalent distance in water between the effective section and the transducer is thus equal to 40.8+104.85=145.65 mm, which corresponds on the graph of FIG. 11 to a radius of the effective section equal to 4.58 mm. The size of the dead zone is equal to 10.71−4.58=6.13 mm.

The straight line plotting variation in the radiation of the effective section of the beam 20 as a function of the penetration depth of the beam depends only on the characteristics of the transducer 18 used, so this line enables the extent of the lateral shadow zone of a part 12 to be determined for a water column 24 of given value and for a given depth within the part.

What is claimed is:

1. A method of determining the extent of a lateral shadow zone corresponding to an edge of a part, in a method of inspecting the part in immersion with at least one ultrasound beam emitted by a transducer oriented perpendicularly to a surface of the part, the transducer being at a predetermined distance from the surface of the part, the method comprising:

measuring the amplitude of an echo of the ultrasound beam as a function of the distance of the axis of the ultrasound beam from an edge of the part or from an edge of a beam deflector element disposed on the surface of the part;

determining the effective section of the ultrasound beam from variations in the amplitude of the echo of the ultrasound beam as a function of the distance of the axis of the ultrasound beam from the edge of the part or from the edge of the beam deflector element; and determining the extent of the shadow zone from the effective section of the ultrasound beam, the extent of the shadow zone for the determined distance between the transducer and the surface of the part being equal to the radius of the effective section of the beam at the surface of the part.

2. A method according to claim 1, further comprising measuring the variation in the echo amplitude at the reflection of the beam on the surface of the part as a function of the distance between the axis of the beam and the edge of the part, the distance between the transducer and the surface of the part being constant.

3. A method according to claim 2, further comprising:

measuring the distance $d_1$ between the axis of the beam and the edge of the part from which the echo amplitude begins to decrease when the distance $d_1$ from the edge of the part decreases;

measuring the distance $d_2$ between the axis of the beam and the edge of the part at which said amplitude becomes zero; and obtaining the size of the shadow zone from the edge of the part by calculating the value $(d_1+d_2)/2$.

4. A method according to claim 3, further comprising:

measuring the distance of the axis of the beam from the edge of the part when the echo amplitude is equal to a small fraction of the maximum value of said amplitude; and determining the distance $d_2$ between the axis of the beam and the edge of the part at which said amplitude becomes zero by extrapolation.

5. A method according to claim 4, wherein said measuring of the distance of the axis of the beam from the edge of the part is performed when the echo amplitude is equal to a few percent of the maximum value of said amplitude.

6. A method according to claim 1, wherein the transducer is oriented perpendicularly to the surface of the part away from the shadow zone, and the method further comprises:

moving the beam deflector element in translation on said surface along an axis that intersects the axis of the ultrasound beam; and identifying the positions of said element at which the echo amplitude of the beam at the reflection on the surface of the part varies between a maximum value and a zero value.

7. A method according to claim 6, wherein the deflection element is a prism presenting at least one reflection face that is inclined to the surface of the part and to the axis of the beam.

8. A method according to claim 7, further comprising:

identifying the two diametrically opposite positions of the prism about the axis of the ultrasound beam for which the echo amplitude of the beam at the reflection on the surface of the part begins to decrease from a maximum value on moving the prism closer to the axis of the beam; and calculating half of the distance between these two positions in order to obtain the extent of the lateral shadow zone.

9. A method according to claim 7, wherein said at least one reflection face is inclined at 45° to the surface of the part and to the axis of the beam.

10. A method according to claim 1, further comprising:

aligning the emission axis of the transducer on a calibration hole formed in the part outside the shadow zone; and measuring the variation in the echo amplitude of the beam at the reflection on the end wall of the calibration hole while the beam is being progressively intercepted by the deflector element.

11. A method according to claim 1, further comprising:

determining the size of the lateral shadow zone on a calibration part having identical flat-ended holes formed to the same depth and at different distances from the edges of the part, one of the holes being outside the shadow zone and the other holes being in said zone;

aligning the transducer on each hole in succession and in measuring the echo amplitude of the beam at the reflection on the end wall of the hole;

plotting the curve showing variation in said amplitude between a maximum value and a zero value as a function of the distance between the axes of the holes and the edges of the part; and deducing the size of the shadow zone as being equal to the value of the distance at which said amplitude begins to decrease with decreasing distance between the axes of the holes and the edges of the part.

12. A method according to claim 11, wherein the end wall of each hole is situated beside the surface of the part and each hole opens out into the opposite surface of the part.

13. A method according to claim 1, further comprising determining a linear variation in the radius of the effective section of the ultrasound beam as a function of the penetration depth of said beam in the part on the basis of:

a maximal value for the radius corresponding to a zero distance between the transducer and the part at which the radius of the effective section at the surface of the part is equal to the radius of the transducer; and a minimal value of the radius at a depth in the part corresponding to the focal length of the transducer.

14. A method according to claim 13, further comprising, for a given distance between the transducer and the part and for a given depth within the part, calculating the extent of the lateral shadow zone by taking the difference between the radius of the effective section of the beam at the surface of the part and the radius of the effective section at the depth under consideration.

15. A method according to claim 13, further comprising:

determining the minimal value of the radius of the effective section of the beam by placing the transducer at a distance from the surface of the part that corresponds to its focal length; and measuring the radius of the effective section of the beam at the surface of the part.

16. A method according to claim 1, wherein said measuring of the amplitude of the echo of the ultrasound beam is performed as a function of the distance of the axis of the ultrasound beam from the edge of the part, and wherein said determining of the effective section of the ultrasound beam is performed from variations in the amplitude of the echo of the beam as a function of the distance of the axis of the ultrasound beam from the edge of the part.

17. A method according to claim 1, wherein said measuring of the amplitude of the echo of the ultrasound beam is performed as a function of the distance of the axis of the ultrasound beam from the edge of the beam deflector element disposed on the surface of the part, and wherein said determining of the effective section of the ultrasound beam is performed from variations in the amplitude of the echo of the ultrasound beam as a function of the distance of the axis of the ultrasound beam from the edge of the beam deflector element.

* * * * *